(12) United States Patent
Kirschman (10) Patent No.: US 10,182,849 B2
(45) Date of Patent: *Jan. 22, 2019

(54) SPINAL IMPLANT LOCKING MEMBER WITH IMPROVED GUIDANCE, TACTILE AND VISUAL FEEDBACK

(71) Applicant: X-spine Systems, Inc., Miamisburg, OH (US)

(72) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/283,492

(22) Filed: Oct. 3, 2016

(65) Prior Publication Data

US 2017/0020575 A1    Jan. 26, 2017

Related U.S. Application Data (63) Continuation of application No. 14/456,171, filed on Aug. 11, 2014, now Pat. No. 9,456,850, which is a continuation of application No. 12/641,416, filed on Dec. 18, 2009, now Pat. No. 8,801,761.

(51) Int. Cl.
| | | |
|---|---|---|
| A61B 17/70 | (2006.01) | |
| A61B 17/86 | (2006.01) | |
| A61B 17/56 | (2006.01) | |
| A61B 17/68 | (2006.01) | |

(52) U.S. Cl.
CPC ...... *A61B 17/7037* (2013.01); *A61B 17/7032* (2013.01); *A61B 17/8665* (2013.01); *A61B 2017/567* (2013.01); *A61B 2017/681* (2013.01); *A61B 2017/868* (2013.01); *A61B 2017/8675* (2013.01)

(58) Field of Classification Search
CPC .. A61B 17/70; A61B 17/7032; A61B 17/7037
See application file for complete search history.

(56) References Cited

U.S. PATENT DOCUMENTS

| | | | | |
|---|---|---|---|---|
| 6,899,714 | B2 * | 5/2005 | Vaughan | A61B 17/1757 606/264 |
| 8,801,761 | B2 * | 8/2014 | Kirschman | A61B 17/7032 606/302 |
| 9,456,850 | B2 * | 10/2016 | Kirschman | A61B 17/7032 |
| 2004/0260283 | A1 * | 12/2004 | Wu | A61B 17/7032 606/270 |
| 2006/0036244 | A1 * | 2/2006 | Spitler | A61B 5/103 74/1 R |
| 2008/0183215 | A1 * | 7/2008 | Altarac | A61B 17/7005 606/265 |
| 2008/0294203 | A1 * | 11/2008 | Kovach | A61B 17/7032 606/308 |

* cited by examiner

Primary Examiner — Christopher Beccia
(74) Attorney, Agent, or Firm — Sheridan Ross P.C.

(57) ABSTRACT

An implant having a receiver that is adapted to receive a polyaxial screw in the bore and either an internal or external cap. The cap can be an external or internal cap and the implant further has at least one locking aid in the form of at least one of a tactile feedback, a visual feedback or an enhanced fixation between the cap and a rod that is received in the receiver.

23 Claims, 6 Drawing Sheets

SPINAL IMPLANT LOCKING MEMBER WITH IMPROVED GUIDANCE, TACTILE AND VISUAL FEEDBACK

CROSS-REFERENCE TO RELATED APPLICATION

This application is a continuation of U.S. patent application Ser. No. 14/456,171, filed Aug. 11, 2014, which issues as U.S. Pat. No. 9,456,850 on Oct. 4, 2016, which is a continuation of U.S. patent application Ser. No. 12/641,416, filed Dec. 18, 2009, now issued as U.S. Pat. No. 8,801,761, all of which are incorporated herein by reference and made a part hereof.

BACKGROUND OF THE INVENTION

1. Field of the Invention

This invention relates to a spinal implant system and method and, more particularly, to an implant having and a lock aid that provides at least one of improved guidance, tactile or visual feedback or enhanced fixation and locking of a cap in a receiver of the implant.

2. Description of the Related Art

Spinal implant screws, such as those used in the pedicles of the thoracic and lumbar spines are commonly used today by spinal surgeons. In a typical prior art screw, there are three main components: a screw shaft, a polyaxial tulip head or receiver incorporating a female thread, and a locking cap incorporating a male thread. The purpose of the threaded locking cap is to affix a spinal stabilizing element, typically a cylindrical rod, to the screw assembly.

During the surgical procedure the surgeon must forcefully seat the rod into the tulip via rotation of the locking cap. Such seating affects the desired correction of the spine. Therefore, the threads of the locking cap and tulip must bear high torque loading which can result in cross-threading and/or thread failure upon initial thread engagement.

Furthermore, the cap may be difficult to engage in the tulip or receiver under such conditions because the thread start-point of both the male and female threads are difficult to identify in a surgical environment. In standard threading, there is little, if any, tactile feedback that the thread is engaged. These problems are exacerbated by the necessity to make thread dimensions very small in order to limit the size of the implant due to anatomical constraints.

Due to such size constraints and strength requirements, a thread with depth greater than thread width is desirable. However, such threads are typically difficult to engage What is needed, therefore, is a spinal implant incorporating a thread design that prevents cross threading of the small-pitch threads of the locking cap/tulip pair, achieves high connection strength immediately after initial thread engagement and offers improved tactile feedback of thread engagement to the surgeon.

Utilizing blunt-tip threads for the prevention of cross threading was first invented by Higbee in 1891 (U.S. Pat. No. 447,775). Myriad spinal screw designs have been put forth, exemplified by U.S. Pat. No. 5,474,555, however none address the combined issues of threaded cap guidance, visual feedback, and tactile feedback. All of these patents are incorporated herein by reference and made a part hereof.

Some prior art polyaxial screw designs are shown and identified in U.S. Patent Publication Nos. 2007/0043357, 2007/0123867, 2006/0155278, 2007/0123862, 2007/0093827, 2008/0071277, 2008/0097457 and 2008/0249576, all of which are incorporated herein by reference and made a part hereof.

What is needed, therefore, is a system and method that improves the polyaxial screw by providing at least one improved locking aid in the form of at least one of a visual feedback, tactile feedback or enhanced fixations or locking of the cap on the tulip.

SUMMARY OF THE INVENTION

It is, therefore, one object of the embodiment to provide an improved polyaxial screw.

Another object of the embodiment is to provide an improved polyaxial screw having at least one of visual feedback, tactile feedback or enhanced locking to facilitate providing a locking aid.

Still another object of the embodiment is to provide a cap that comprises a surface for facilitating guiding and mounting the cap on the receiver.

Another object of one embodiment is to provide a cap having indicia for indicating a start of a thread used to thread the cap on the receiver or tulip.

Still another object of one embodiment is to provide a cap comprising at least one deformable area, such as a deformable ring, for facilitating locking the cap on the receiver and thereby locking a rod to a screw.

Another object of one embodiment is to provide a polyaxial screw that can utilize one or more of the locking aids described herein.

In one aspect, one embodiment comprises an implant comprising a receiver having at least one internal wall defining a bore, at least a portion of the receiver having a receiver thread, the receiver further comprising a rod-receiving channel in communication with the bore, the rod-receiving channel being adapted to receive a rod, a polyaxial screw for receipt in the bore, a cap having a cap thread for mating with the receiver thread to permit the cap to be screwed on the receiver in order to lock the rod in the rod-receiving channel of the receiver, and a lock aid associated with at least one of the receiver or the cap for facilitating providing at least one of a tactile feedback when the cap is mounted on the receiver, a visual feedback for facilitating mounting the cap on the receiver, or an enhanced fixation between the cap and the rod when the cap is received on the receiver.

In another aspect, another embodiment comprises an implant cap for mounting on an implant receiver that receives and supports a rod in a rod-receiving area of the implant receiver and that has receiver threads, the implant cap comprising a body having an area for receiving a tool for rotatably driving the implant cap, a cap thread for cooperating with the receiver thread to permit the implant cap to be screwed and mounted on or in the implant receiver in order to lock the rod in the rod-receiving area of the implant receiver, and a lock aid for providing at least one of tactile feedback, visual feedback or enhanced fixation when the implant cap is screwed on the implant receiver.

In still another aspect, another embodiment comprises an implant comprising a receiver having a at least one internal wall defining a bore, at least a portion of the receiver having a receiver thread, the receiver further comprising a rod-receiving channel in communication with the bore, the rod-receiving channel being adapted to receive a rod, a polyaxial screw for receipt in the bore, a cap having a cap thread for mating with the receiver thread to permit the cap to be screwed on the receiver in order to lock the rod in the rod-receiving channel of the receiver, and the receiver thread is defined by a female thread, a leading portion of the female thread being truncated or cut out.

In still another aspect, another embodiment comprises an implant comprising a receiver having a at least one internal wall defining a bore, at least a portion of the receiver having a receiver thread, the receiver further comprising a rod-receiving channel in communication with the bore, the rod-receiving channel being adapted to receive a rod, a polyaxial screw for receipt in the bore, a cap having a cap thread for mating with the receiver thread to permit the cap to be screwed on the receiver in order to lock the rod in the rod-receiving channel of the receiver, and the cap comprising a surface for facilitating guiding the cap on the receiver and aligning the cap thread with the receiver thread so that the cap can be screwed on the receiver.

In still another aspect, another embodiment comprises an implant comprising a receiver having a at least one internal wall defining a bore, at least a portion of the receiver having a receiver thread, the receiver further comprising a rod-receiving channel in communication with the bore, the rod-receiving channel being adapted to receive a rod, a polyaxial screw for receipt in the bore, and a cap having a cap thread for mating with the receiver thread to permit the cap to be screwed on the receiver in order to lock the rod in the rod-receiving channel of the receiver, the cap comprises a deformable area adapted to engage the rod and deforming on it after the rod is received in the receiver and the cap is screwed on the receiver.

These and other objects and advantages of the invention will be apparent from the following description, the accompanying drawings and the appended claims.

DETAILED DESCRIPTION OF THE PREFERRED EMBODIMENTS

Figure 1:
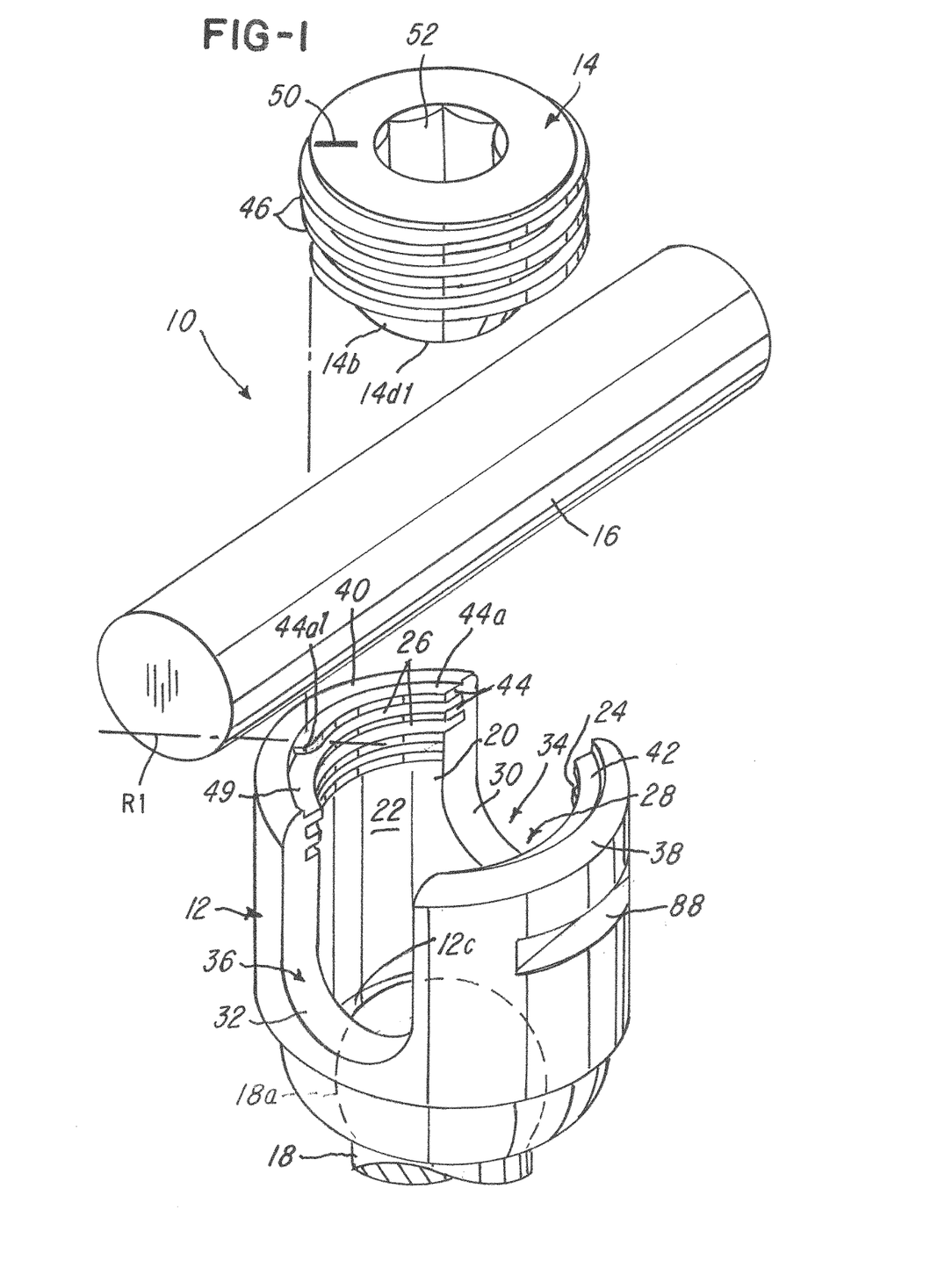
FIG. 1 is a exploded view of one embodiment of the invention.

Referring now to FIGS. 1-10, an implant, polyaxial screw, system and method 10 are shown. In a first illustrative embodiment, the system 10 comprises a receiver 12 and a cap 14 which is threadably mounted on the tulip or receiver 12. The receiver 12 receives the cap 14 after a rod 16 and a polyaxial screw 18 are received in the receiver 12 in a manner conventionally known and as shown in FIG. 1.

The receiver 12 comprises at least one internal wall 20 defining a bore 22. At least a portion of the receiver 12 comprises a plurality of female threads, such as threads 24 and 26. In this regard, note that the receiver 12 comprises a rod-receiving channel 28. The receiver 12 comprises a first generally U-shaped wall 30 that defines a first rod-receiving opening 34 and a generally opposed second generally U-shaped wall 32 that defines a second rod-receiving opening 36 as shown. The first and second rod-receiving openings 34 and 36 cooperate to define the rod-receiving channel 28 for receiving the rod 16. Note that the receiver 12 further comprises a first arcuate wall 38 and a generally opposing second arcuate wall 40 that lie between the first and second rod-receiving openings 34 and 36 as shown.

The first arcuate wall 38 comprises first arcuate wall threads 42 and the second arcuate wall 40 comprises second arcuate wall threads 44 as shown. The first and second arcuate wall threads 42 and 44 cooperate to define the receiver threads for threadably receiving male cap threads 46 on the cap 14 so that the cap 14 can be screwed onto the receiver 12 in order to lock the rod 16 in the rod-receiving channel 28 of the receiver 12.

The implant and system 10 comprises at least one or a plurality of lock aids associated with at least one of the receiver 12 or cap 14 for facilitating providing at least one of a tactile feedback system, method or means when the cap 14 is mounted on the receiver 12, a visual feedback system, method or means for facilitating aligning and/or mounting the cap 14 on the receiver 12 or an enhanced fixation system, method or means between the cap 14 and the rod 16 when the cap 14 is threadably received on the receiver 12.

In one illustrative embodiment, the lock aid comprises the tactile feedback system, method or means mentioned. In this regard, note in FIG. 1 that the first thread 44a of the second arcuate wall threads 44 defines a starting thread that is shorter than at least one other of the second arcuate wall threads 44 in order to define a cut-out area 49 for facilitating receiving a leading edge portion 46a (FIG. 3) of a male thread of the male cap thread 46. The surgeon or user can feel the cap 14 drop down into the receiver 12 when the leading edge portion 46a is aligned with the cut-out area 49. This design provides tactile feedback when the cap 14 is received on the receiver 12. This feature is particularly useful during surgery where sometimes it is difficult for the surgeon to see the cap 14 relative to the receiver 12. In the illustration being shown, the leading edge portion 46a of the male cap thread 46 may be identified with indicia 50 which provides the visual feedback of the location of the leading edge portion 46a of the cap 14. The cut-out area 49 and its cooperation and reception of the leading edge portion 46a are adapted to permit the drop down and define the lock aid.

Figure 3:
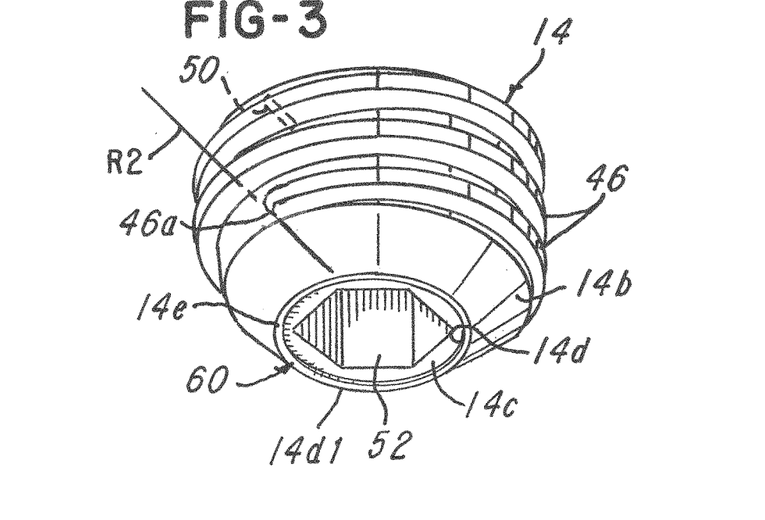
FIG. 3 is a view of a cap illustrating a guiding surface.

Notice in FIG. 3 that the leading edge portion 46a of the male cap thread 46 is truncated as shown. Likewise, the leading edge portion 44a1 of the first thread 44a is also truncated. In one illustrative embodiment, the leading edge portion 44a1 of the first thread 44a of the receiver 12 and the leading edge portion 46a of the male cap thread 46 of the cap 14 are truncated and adapted so that when these leading edge portions 44a1 and 46a are adjacent each other and initially pass each other when the cap 14 is mounted on the receiver 12, the leading edge portions 44a1 and 46a move relative to each other a drop down distance DD (FIG. 4), which in the illustration being described is greater than at least one thread pitch associated with the second arcuate wall threads 44. It should be understood that the leading edge portion 44a1 lies along the first radial line R1 (FIG. 1), and the leading edge portion 46a of the male cap thread 46 on the cap 14 lies along a second radial line R2 (FIG. 3). In the illustration being described, note that the first radial line R1 is generally perpendicular to an axis of the receiver 12 and the leading edge portion 46a that lies in along the second radial line R2 is generally perpendicular to an axis of the cap 14. Note also that in the illustration being described, the first and second radial lines R1 and R2 become generally parallel when the first and second leading edge portions 44a1 (FIG. 1) and 46a (FIG. 3) initially align when the cap 14 is mounted on the receiver 12.

Figure 5:
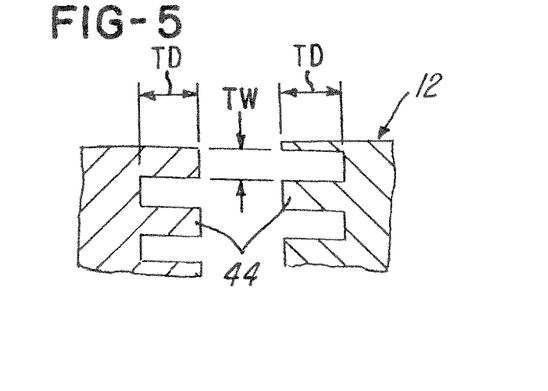
FIG. 5 is a fragmentary sectional view showing various details of the female threads in the receiver.

As illustrated in FIG. 5, note that the second arcuate wall threads 44 on the receiver 12 comprise a thread depth TD (FIG. 5) that is greater than a thread width TW as shown. It has been found that this relative relationship of the thread depth TD to the thread width TW further facilitates providing the tactile feedback and locking of the cap 14 in the receiver 12. In the illustration being described, the second arcuate wall threads 44 comprise at least a portion having the thread depth TD that is greater than at least one of the thread width or pitch and is adapted to define the lock aid.

As mentioned earlier, the cap 14 comprises the indicia 50 which is aligned with the leading edge portion 46a (FIG. 3) that provides a visual notice or feedback of the leading end portion 46a, which also provides a locking aid to the user. In the illustration being described, the indicia 50 may be an engraved or embossed or raised mark or indicia or it could be a permanent marking on the surface 14a of the cap 14.

Returning to FIG. 4, note that the drop down distance DD is greater than a cumulative distance between a pitch between adjacent threads of the second arcuate wall threads 44 and is also greater than the thread width TW (FIG. 5).

Figure 4:
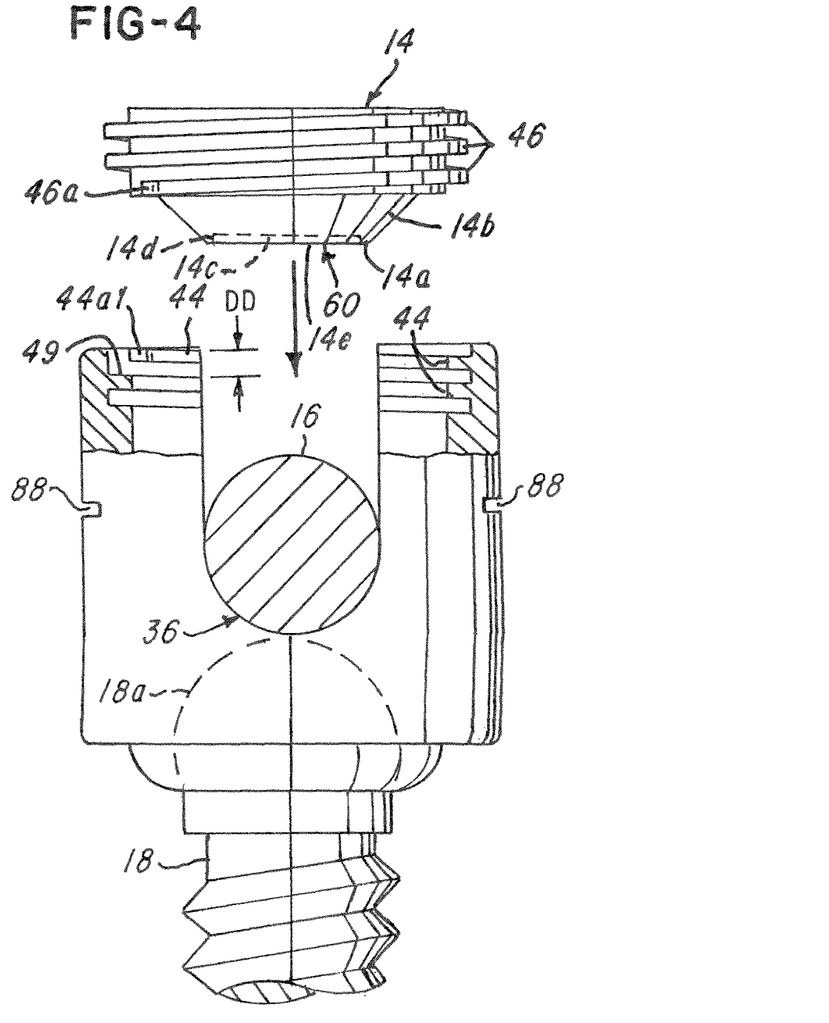
FIG. 4 is a view illustrating a drop down distance and the mounting of the cap on a receiver or tulip.

As illustrated in FIGS. 1, 3 and 4, note that a bottom 14b of the cap 14 has a surface that is adapted to provide the lock aid by facilitating guiding the cap 14 on the receiver 12 to facilitate aligning the cap 14 and the male cap threads 46 and the leading edge portion 46a with the cut-out area 49 of the receiver 12 so that the cap 14 can be easily guided and screwed onto the receiver 12. In the embodiment being described, notice that the bottom 14b is frusto-conical, but it should be understood that the surface shape could be any suitable shape adapted to guide the cap 14 into the bore 22 and onto the receiver 12. For example, the surface could have an arcuate, curved or semi-spherical shape such that the bottom 14b is adapted to facilitate aligning and guiding the cap 14 onto the receiver 12 so that the cap 14 can be easily screwed onto the receiver 12.

Figure 6:
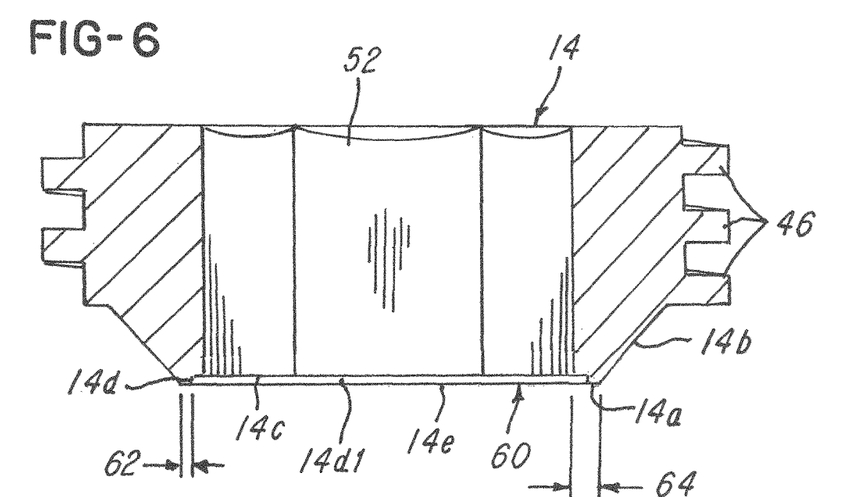
FIG. 6 is fragmentary sectional view of the cap shown in FIGS. 3 and 4.

In the illustration being described, notice that the bottom 14b terminates at an end 14c (FIG. 6). In the illustration being described, the cap 14 has a tool-receiving opening 52 (FIG. 2) for receiving a tool for rotatably driving the cap 14. In the illustration being shown, the tool is a hex wrench (not shown), but it could be any suitable tool adapted to rotatably drive the cap 14.

Figure 2:
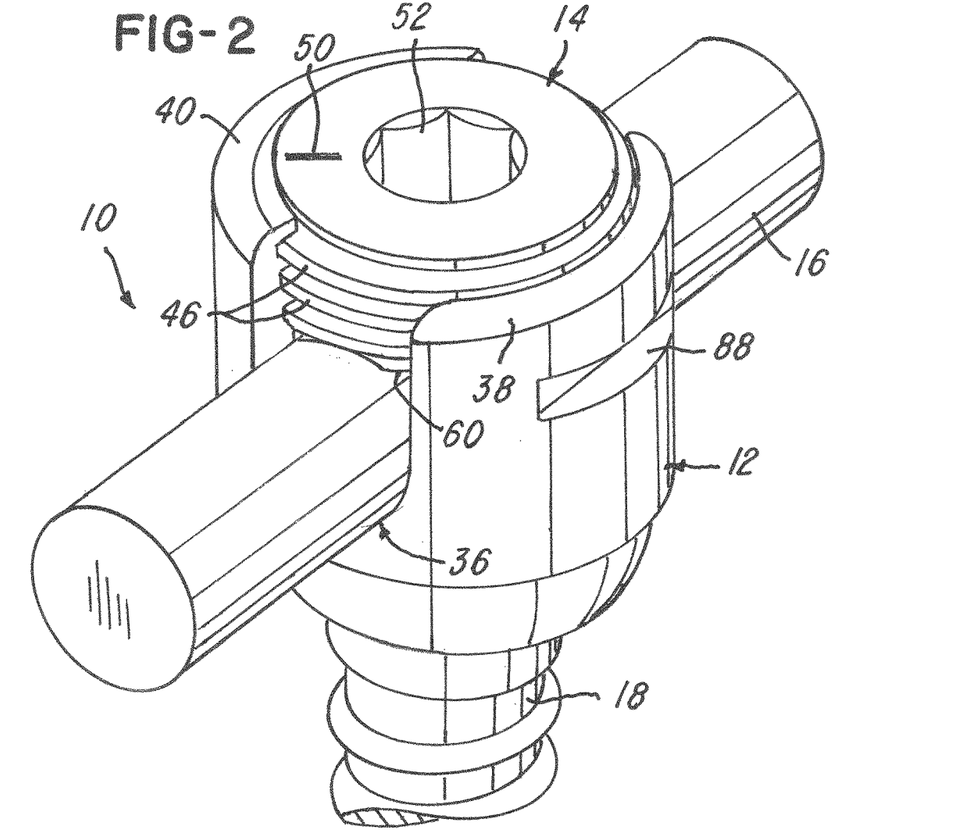
FIG. 2 is an assembled view of the embodiment shown in FIG. 1.
Figure 7:
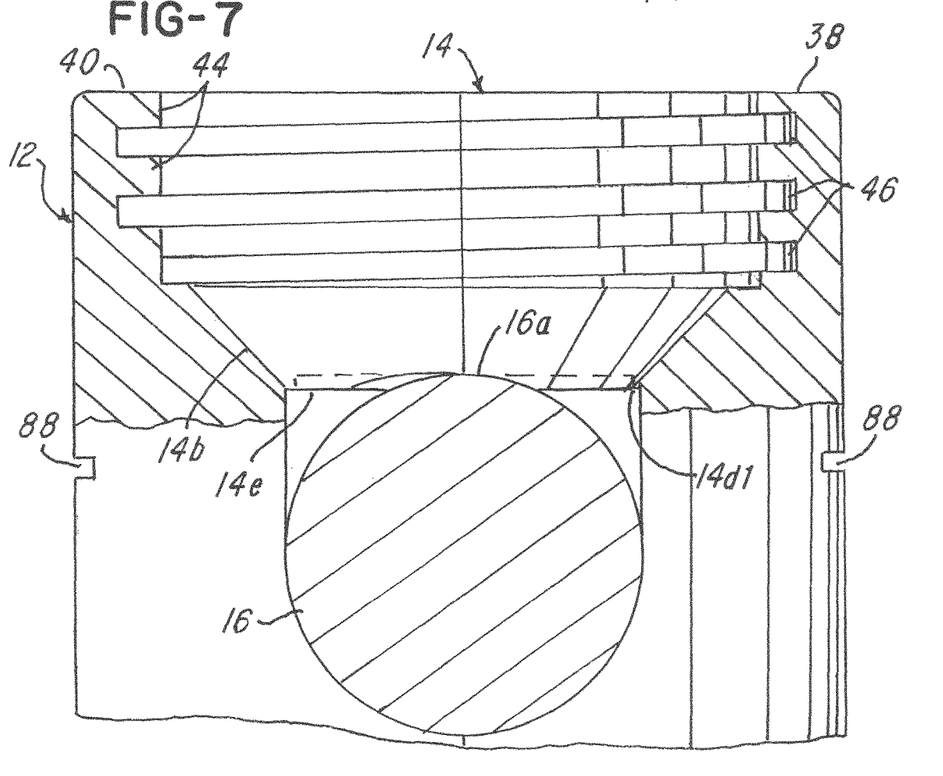
FIG. 7 is a view of a deformation of at least a portion of the cap as it engages the rod.

Returning to FIGS. 3, 4 and 6, note that the cap 14 comprises a deformable area 60 that is adapted to provide the lock aid. In the illustration being described, the deformable area 60 comprises a deformable ring 14d that is monolithically and integrally formed with the cap 14, as best illustrated in FIG. 6. As shown in FIG. 2, the cap 14 is received on the receiver 12 and screwed into the receiver 12 until a bottom edge or surface 14e engages the rod 16. The deformable ring 14d and the deformable area 60 deforms about the rod 16 as the cap 14 is screwed into the receiver 12 and as it compresses against the rod 16 as illustrated in FIGS. 2 and 7. The engagement of the surface 14d1 against the rod surface 16a provides a friction engagement and causes the surfaces to become cold-welded in the illustration. In one illustrative embodiment, the monolithic ring comprises a width of between 0.120-0.280 inches.

In the illustration being described, it should be understood that the cap 14 engages and becomes cold-welded onto the receiver 12 in less than or equal to about two-and-one-half turns of the cap 14 after the cap 14 is received in the receiver 12. Also, the deformable ring 14d and deformable area 60 become cold-welded or secured to or against the rod 16 in less than one full turn of the cap 14 after the surface 14e engages the rod 16. Advantageously, the locking of the rod 16 onto a head 18a of the polyaxial screw 18 has been achieved with less than three or even two-and-one-half turns of the cap 14 in the receiver 12 as mentioned. This reduces the overall length of the cap 14 and the receiver 12, while achieving locking of the rod 16 to the head 18a with an equivalent or even greater amount of locking strength than the locking devices used in the past.

As best seen in FIGS. 3 and 6, note that the locking ring 14d comprises a locking ring wall or surface 14d1 (FIG. 6) that is generally parallel to an axis of the cap 14 and generally perpendicular to the end 14c as shown. Note also that the surface 14d1 comprises a thickness or dimension 62 which is generally smaller than a cross-sectional thickness 64 of the dimension defined by an inner surface 14a and the bottom 14b, as illustrated in FIG. 6. This dimension 62 is adapted and selected to enable the deformable ring 14d or deformable area 60 to deform, while the end 14c remains undeformed as shown in FIG. 7. In the illustration being described, the deformable ring 14d provides an enhanced fixation or even a cold-weld between the cap 14 and the rod 16 when the cap 14 is received on the receiver 12.

Advantageously, the implant, system and method 10 described herein provide an improved implant with a locking aid that can comprise the tactile feedback, visual feedback or enhanced fixation either individually or in any combination desired.

During use, the polyaxial screw 18 is received in the bore 22 and the head 18a is received in a seat 12c of the receiver 12. The polyaxial screw 18 is screwed into bone and the receiver 12 receives the rod 16 and the receiver 12 and rod 16 are positioned in a manner conventionally known. The cap 14 is received on a tool and the user guides the cap 14 into the bore 22 using the tactile feedback that the bottom 14b provides as it engages and guides the cap 14 as it engages the second arcuate wall threads 44 in the receiver 12 and guides the cap 14 into alignment for threading in the receiver 12. After the positioning is achieved, the surgeon or user may use the at least one or a plurality of the tactile feedback in the form of the truncated leading edge portion 46a and which is aligned in the cut-out area 49. The user may use the indicia 50 to facilitate aligning the thread and the tactile feedback of the cap 14 dropping down in the receiver 12 the drop down distance DD (FIG. 4) as the cap 14 is positioned on the receiver 12.

After the cap 14 is mounted on the receiver 12 it is screwed using the tool (not shown) until the deformable ring 14d deforms on the rod 16, thereby providing the enhanced fixation by deforming on the rod 16, thereby locking the rod 16 against the head 18a of the polyaxial screw 18.

Although not shown, it should be appreciated that other conventional components may be used with the receiver 12, such as an internal compression member (not shown) that is situated between the rod 16 and the head 18a.

Figure 8:
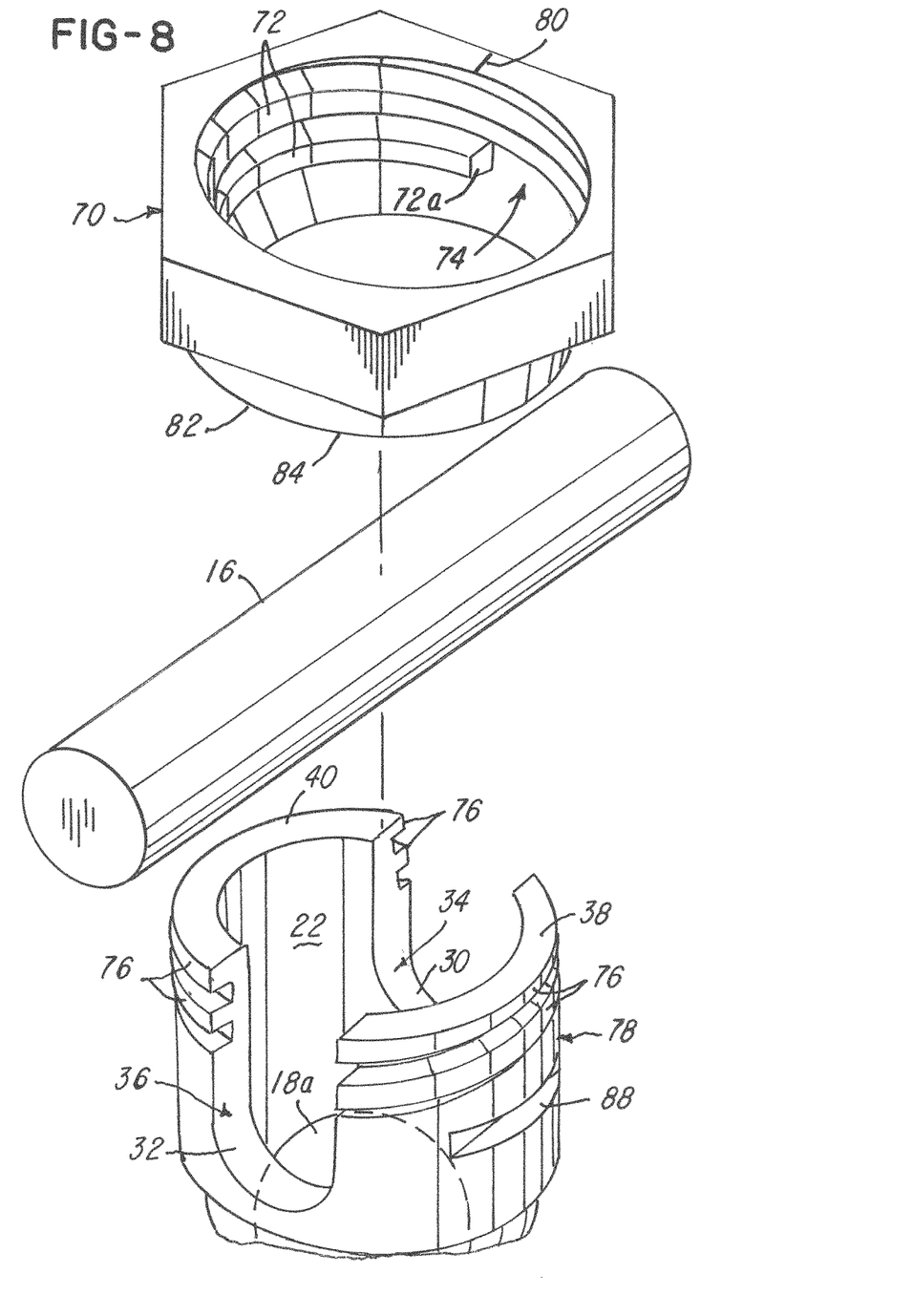
FIG. 8 is an exploded view of another embodiment illustrating an external cap.
Figure 9:
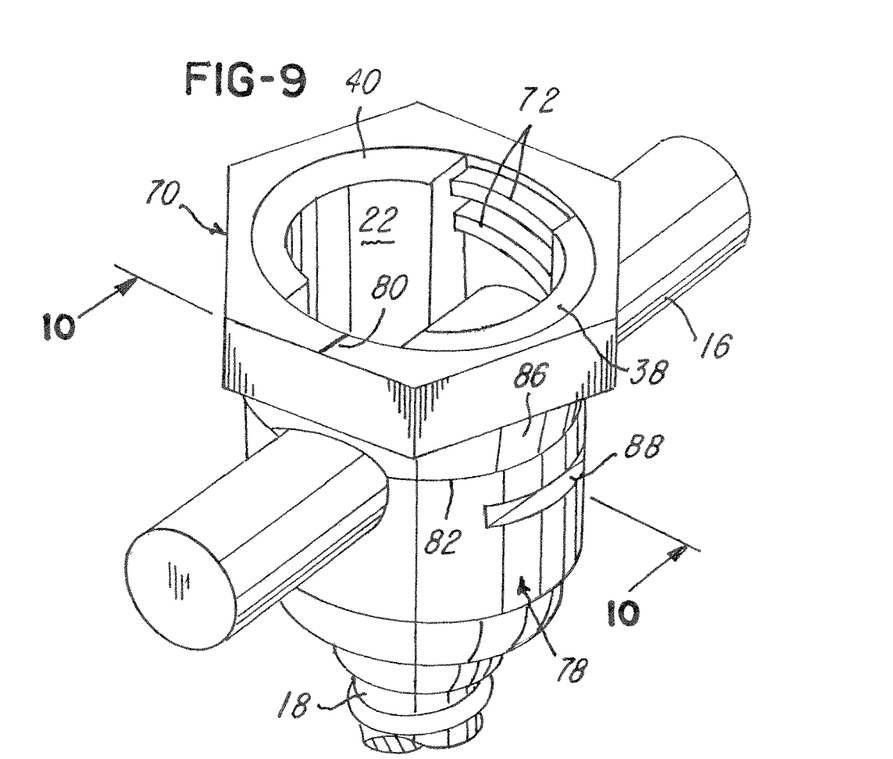
FIG. 9 is an assembled view of the embodiment shown in FIG. 8.

Advantageously, the implant, system and method 10 described herein provides an enhanced or improved locking of the rod 16 on the receiver 12. This embodiment has been shown with the internal cap 14. FIGS. 8 and 9 illustrate another embodiment of the invention with like parts having the same part numbers.

Figure 10:
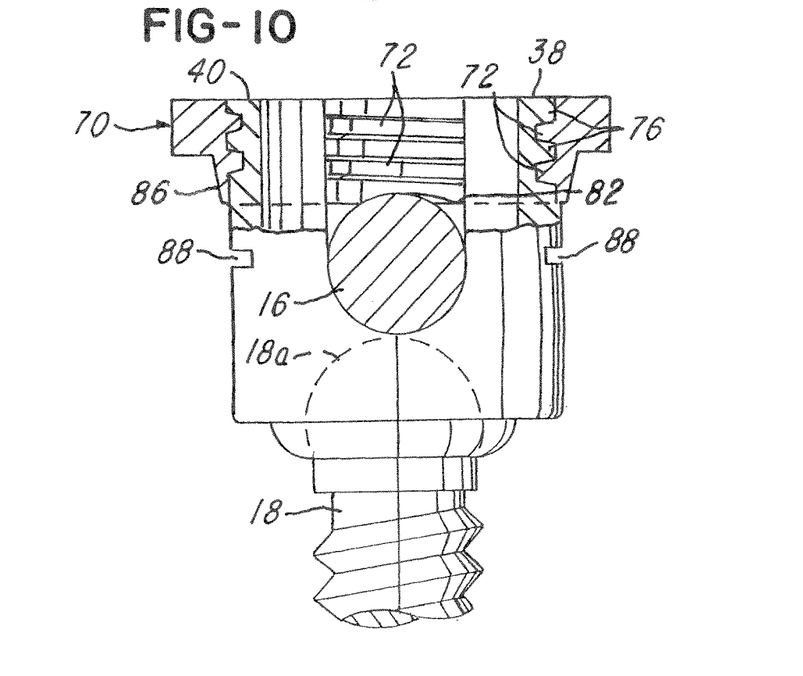
FIG. 10 is a fragmentary sectional view taken along the line 10-10 in FIG. 9.

In the embodiment of FIGS. 8-10, an external cap 70 having a plurality of internal threads 72 and a receiver 78 are shown. The threads 72 have at least one thread that is truncated in the manner described earlier herein relative to the second arcuate wall threads 44. Notice that the end portion 72a (FIG. 8) of the internal thread 72 is truncated and performs the same or similar function as the leading edge portion 44a1 (FIG. 1) in the embodiment described earlier herein. In this regard, notice that the truncated portion of thread 72 defines a cut-out area 74 (FIG. 8) for facilitating receiving and starting male threads 76 on the receiver 78. As with the prior embodiment, the cap 70 may comprise an indicia 80 (FIG. 9) for providing a visual aid or guide as to the start of the end portion 72a as shown.

As with the embodiment described earlier herein, note that the embodiment of FIGS. 8 and 9 also comprises a deformable area 82 (FIGS. 8-10) in the form of a monolithic deformable ring 84 that is adapted and dimensioned to deform about the rod 16, as illustrated in FIGS. 9 and 10, when the cap 70 is screwed onto the receiver 78 as illustrated. In this regard, the deformable area 82 comprises the monolithic and integrally formed ring 84 that is similar in shape and construction to the deformable ring 14d described earlier herein relative to FIG. 4. As illustrated in FIG. 10, notice that the cap 70 comprises a frusto-conical surface 86 which facilitates guiding the cap 70 onto the receiver 12 similar to the bottom 14b of the embodiment described earlier herein.

Thus, as with the embodiment described earlier, the embodiment shown in FIGS. 8-10 provide the locking aid that comprises at least one or a plurality of the tactile feedback, visual feedback and enhanced fixation between the cap 70 and the receiver 78 to facilitate locking of the rod 16 and polyaxial screw 18 in the receiver 78.

In the illustrations being described, the receivers 12 and 78 may comprise notched out areas 88 (FIGS. 2 and 9) for enabling the user or surgeon to position or hold the receiver 12 using a conventional fork tool (not shown).

While the system, apparatus and method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. An implant comprising:
   a receiver having at least one internal wall defining a bore adapted to receive a polyaxial screw, at least a portion of said receiver having a receiver thread, said receiver further comprising a rod-receiving channel in communication with said bore, said rod-receiving channel being adapted to receive a rod, wherein the rod contacts at least a portion of a head of the polyaxial screw; and
   a cap having a cap thread for mating with said receiver thread to permit said cap to be screwed on said receiver in order to lock said rod in said rod-receiving channel of said receiver, wherein the cap contacts at least a portion of the rod;
   wherein said cap comprises an aperture in a rod-engaging end, said cap having a monolithic and deformable ring surrounding said aperture that is adapted to engage said rod and deform on it after said rod is received in said receiver and said cap is screwed on said receiver, and wherein said cap comprises a deformable area, said deformable area engaging said rod and deforming on it after said rod is received in said receiver and said cap is rotated and screwed on said receiver.

2. The implant as recited in claim 1 wherein said receiver thread is defined by a female thread, a leading portion of said female thread being truncated or cut out and adapted to define a lock aid.

3. The implant as recited in claim 2 wherein said cap thread is defined by a male thread, a leading portion of said male thread being truncated or cut out and adapted to define said lock aid.

4. The implant as recited in claim 3 wherein said leading portion of said female thread of said receiver and said leading portion of said a male thread of said cap each being truncated and adapted so that when said leading portions are adjacent each other and initially pass each other when said cap is mounted on said receiver, said leading portions move relative to each other a drop-down distance that is greater than or equal to at least one thread pitch.

5. The implant as recited in claim 3 wherein said leading portion of said female thread lies along a first radial line that is generally perpendicular to an axis of said receiver and said leading portion of said male thread lies along a second radial line that is generally perpendicular to an axis of said receiver, said first and second radial lines being generally parallel when said leading portions initially align when said cap is mounted on said receiver.

6. The implant as recited in claim 1 wherein said receiver thread comprises at least a portion having a thread depth that is greater than a thread width.

7. The implant as recited in claim 1 wherein said rod-receiving channel comprises a first rod-receiving opening and a generally opposed second rod-receiving opening in said receiver, said at least one internal wall comprising a first arcuate wall between said first and second rod-receiving openings and a second arcuate wall that generally opposes said first arcuate wall, said first arcuate wall having first arcuate wall threads and said second arcuate wall having second arcuate wall threads, said first and second arcuate wall threads cooperating to define said receiver thread,
   said first arcuate wall threads having a starting thread that is shorter than at least one other of said first arcuate wall threads to define a cut-out zone for facilitating receiving a starting thread of said cap thread, thereby providing tactile feedback when said cap is received on said receiver.

8. The implant as recited in claim 1 wherein said receiver threads comprise at least a portion having a thread depth that is greater than at least one of a thread width or pitch.

9. The implant as recited in claim 1 wherein said cap thread comprises at least one male thread having a starting end, said cap further comprising an indicia on a surface that provides notice of said starting end.

10. The implant as recited in claim 9 wherein said indicia is a line on a top surface of said cap, said line being generally aligned with said starting end.

11. The implant as recited in claim 1 wherein at least a portion of said receiver thread is adapted on said receiver to permit a start of said cap thread and said cap to drop down a drop down distance in said receiver, said drop down distance being selected to define a lock aid.

12. The implant as recited in claim 11 wherein said drop down distance is greater than or equal to a pitch distance between adjacent threads of receiver thread.

13. The implant as recited in claim 1 wherein said receiver thread are integral with said at least one internal wall and said cap thread is on an inner diameter surface of the cap so that the cap can be screwed onto an outer surface of said receiver, said cap having an integral deformable ring on a bottom surface of said cap.

14. The implant as recited in claim 1 wherein said cap has a guiding surface to facilitate guiding said cap on said receiver to facilitate aligning said cap thread with said receiver thread so that said cap can be screwed on said receiver.

15. The implant as recited in claim 14 wherein said surface is curved, arcuate, frusto-conical or semi-spherical and situated on an end of said cap, said surface being adapted to engage an open end of said receiver and guide said cap thread toward and into engagement with said receiver thread.

16. The implant as recited in claim 1 wherein said monolithic and deformable area becomes cold welded on said rod when said cap has been screwed on said receiver.

17. The implant as recited in claim 1 wherein said cap comprises a cap bottom having a deformable area.

18. The implant as recited in claim 17 wherein said cap bottom is generally planar and said deformable area comprises a monolithic ring having a diameter smaller than that of an overall diameter of said cap.

19. The implant as recited in claim 18 wherein a rod-engaging end of said cap comprises a frusto-conical shape, said monolithic and deformable ring being integral with an end of said frusto-conical shape.

20. The implant as recited in claim 2 wherein said cap comprises a deformable area that engages said rod and deforms on it after said rod is received in said receiver and said cap is screwed on said receiver.

21. The implant as recited in claim 20 wherein said deformable area is a ring formed in a rod-engaging end of said cap.

22. The implant as recited in claim 21 wherein said ring is a monolithic ring formed in said rod-engaging end of said cap.

23. The implant as recited in claim 22 wherein said rod-engaging end of said cap comprises a frusto-conical shape, said monolithic ring is integral with an end of said frusto-conical shape.

* * * * *